US009828452B1

(12) United States Patent
Costa da Silva Pinto et al.

(10) Patent No.: US 9,828,452 B1
(45) Date of Patent: Nov. 28, 2017

(54) PROCESS FOR THE SYNTHESIS OF POLY (VINYL ALCOHOL) AND/OR POLY (VINYL ACETATE) WITH SPHERICAL MORPHOLOGY AND SHELL-AND-NUCLEUS STRUCTURE AND ITS USE IN VASCULAR EMBOLIZATION

(75) Inventors: José Carlos Costa da Silva Pinto, Rio de Janeiro (BR); Mariana Araújo Niemeyer Limeira, Rio de Janeiro (BR); Fabricio Machado Silva, Rio de Janeiro (BR); Priamo Albuquerque Melo, Rio de Janeiro (BR); Márcio Nele De Souza, Rio de Janeiro (BR); Galdêncio Espinosa Lopez, Niterói (BR)

(73) Assignees: INSTITUTO ALBERTO LUIZ COIMBRA DE PÓS-GRADUAÇÃO E PESQUISA DE ENGENHARIA—COPPE, Rio de Janeiro (BR); FIRST LINE INDUSTRIA E COMMERCIA S/A, Rio de Janeiro (BR)

( * ) Notice: Subject to any disclaimer, the term of this patent is extended or adjusted under 35 U.S.C. 154(b) by 1576 days.

(21) Appl. No.: 11/667,524

(22) PCT Filed: Nov. 10, 2005

(86) PCT No.: PCT/BR2005/000231
§ 371 (c)(1),
(2), (4) Date: May 10, 2007

(87) PCT Pub. No.: WO2006/050591
PCT Pub. Date: May 18, 2006

(30) Foreign Application Priority Data

Nov. 11, 2004 (BR) .................................... 0404994

(51) Int. Cl.
*A61K 31/765* (2006.01)
*A61P 35/00* (2006.01)
*A61P 9/00* (2006.01)
*C08F 216/06* (2006.01)

(52) U.S. Cl.
CPC .................................. *C08F 216/06* (2013.01)

(58) Field of Classification Search
CPC ...................................................... C08F 216/06
See application file for complete search history.

(56) References Cited

U.S. PATENT DOCUMENTS

| 2,582,055 | A | * | 1/1952 | Minsk et al. | ................. | 526/212 |
| 3,510,464 | A | * | 5/1970 | Kenji | ................ | 525/62 |
| 3,627,693 | A | * | 12/1971 | Scarpelli | ................ | 428/402.22 |
| 4,463,138 | A | * | 7/1984 | Wu et al. | ................ | 522/5 |
| 6,191,193 | B1 | * | 2/2001 | Lee et al. | ................ | 523/201 |

OTHER PUBLICATIONS

Lyoo Colloid. Polym. Sci. 2002, 280, 835.*

* cited by examiner

*Primary Examiner* — Suzanne Ziska
*Assistant Examiner* — Thurman Wheeler
(74) *Attorney, Agent, or Firm* — Hamre, Schumann, Mueller & Larson, P.C.

(57) ABSTRACT

The present invention describes a process for the synthesis of spherical particles of polyvinyl alcohol—PVA and/or polyvinyl acetate—PVAc with shell nucleus structure from total or partial hydrolysis in a caustic aqueous medium with obtaining particulates of PVA/PVAc with controlled spherical morphology, to be used in vascular embolization.

32 Claims, 12 Drawing Sheets

PROCESS FOR THE SYNTHESIS OF POLY (VINYL ALCOHOL) AND/OR POLY (VINYL ACETATE) WITH SPHERICAL MORPHOLOGY AND SHELL-AND-NUCLEUS STRUCTURE AND ITS USE IN VASCULAR EMBOLIZATION

TECHNICAL FIELD

The innovation here proposed describes a synthesis process of poly (vinyl alcohol)—PVA and/or poly (vinyl acetate)—PVAc spherical particles with shell-and-nucleus structure from total or partial hydrolysis in a caustic aqueous medium, obtaining PVA/PVAc particles with controlled spherical morphology, to be used in vascular embolization.

The process is characterized by the production of PVAc from a vinyl acetate suspension in water e by the PVAc in-situ saponification in caustic aqueous medium, in the same reaction vessel, without the need of PVAc particles separation from the aqueous medium. The process can be realized in one (simultaneous polymerization and saponification) or two (polymerization followed by saponification) steps, where the saponification degree and shell-and-nucleus structure of the final spherical particle can be controlled by the time of saponification e by the simultaneous use of organic solvents during the process. After the polymerization and saponification steps, an additional step of particle surface treating with organic solvents can be realized, with the objective of modifying the superficial properties of the end product. This operation can be realized in-situ or after particles separation and purification. The final particles can then be treated with radioactive sources or thermal process, with the objective of sterilization and use in living beings.

TECHNICAL BACKGROUND

The vascular embolization constitutes an important strategy for combating tumors, aneurysms and artery-venous malformations (AVMs). The technique consists of the finely divided material injection, via catheter, in the blood stream around the tumoral region, in such a way to obstruct mechanically the blood vessels that irrigates the damaged area. In this way, it is obtained an interruption in the nutrient supplying to the tumoral region; which tends to decrease, allowing a tissue recovery after a certain time interval (Kerber et al., 1978).

Since long time, different materials have been proposed in literature with the objective of occluding vascular channels of tumors and AVMs, within the context of embolization. Latchaw and Gold (1979) cite the utilization of metallic coils, silicone rubber, carbon micro-spheres and poly (vinyl alcohol) particles as materials useful in embolization. In all cases, one must observe the compatibility among the granulometry of the injected material and the catheter and vessels diameters, as well the material capacity of being subjected to sterilization procedures.

Among the above mentioned materials, is of note the poly (vinyl alcohol), PVA, which presents a series of interesting properties, such as a high compressibility, good elasticity, biodegradable, and good chemical resistance to acids, bases and detergents (Tadavarthy et al., 1975). In fact, the PVA foams have the capacity of compressing themselves and reassume the original format when in contact with blood, what makes PVA a material with high appealing to the embolization purposes, once the catheter size limits the size of the particles. However, the PVA presents a peculiar aspect in relation to the other polymeric resins, which is the absence of vinyl alcohol monomer in a free state. Basically, the PVA production occurs via hydrolysis or saponification of poly (vinyl acetate) (Marten, 1989). The PVA properties obtained in the hydrolysis depend strongly of the vinyl acetate polymerization step conditions (existence of ramification) and degree of polymer hydrolysis (moles of alcohol group in the chain). Is of note that vinyl acetate is a monomer with strong tendency to ramification during the reaction, resulting in a polymer with weak chemical resistance and highly susceptible to degradation during the hydrolysis step and conversion to poly (vinyl alcohol). To by-pass this obstacle, usually one gets help of performing tests in reduced temperatures, with utilization of alternative initialization mechanisms, as for example, application of ionizing light in ultra-violet region (Yamamoto et al., 1990). It is important to note the PVA synthesis with good solvent resistance and elevated thermal resistance, once the applied polymer as a material for embolization must be stable and resistant to sterilization procedures.

The PVA particles are normally produced from dissolution of PVAc in organic solvents (usually methanol) and posterior caustic treatment (usually employing soda, NaOH). In these conditions PVA is formed, which precipitates. The precipitated material has an irregular shape and presents typical morphology of flocs, as showed in FIG. 1. Thus, the usual process consists in PVAc production, PVAc purification, PVAc solubilization in caustic solvent, PVAc production, separate and purify PVA. It is proposed the PVA production with controlled morphology, as shown in FIG. 2, from vinyl acetate polymerization in aqueous suspension and PVA saponification in the aqueous suspension itself, simultaneously to the PVAc production or in a posterior step, using to this an alkaline aqueous medium.

Yamamoto et al. (1987) produced PVA from a classical PVAc saponification process in classical methanol. The PVAc was produced in emulsion, using a mercury light source to initialize the reaction. In the present invention the PVAc is produced in suspension and the saponification is carried out in-situ, in aqueous medium.

The U.S. Pat. No. 4,863,972 (Itagaki et al., 1989) claims a process to produce reticulate PVA particles, through PVA precipitation in alcoholic solution, being that, the proposed process does not depend on the preparation of PVA solution to particles formation.

Yamamoto et al. (1990) related the production of PVA from aqueous mixture of VAC and potassium persulfate, in presence of mercury light, being the reaction carried out in emulsion. In the process object of the present invention the reaction is carried out in suspension.

Kim and Lee (1992) related the preparation of PVA spherical particles with shell-and-nuclei structure. The particle is prepared from VAC polymerization in suspension, followed by saponification of the spherical PVAc in caustic aqueous medium, with posterior reticulation of PVA promoted by glutaraldehyde and saponification in caustic methanol. In the present invention neither the reticulation is necessarily done, nor the particles separation between different steps. The produced particles of the present invention can have PVA shell and nuclei with different reticulation degrees and yet, the nuclei in PVAc and the shell in PVA.

Derdeyn et al (1995) analyzed various marketed PVAs and showed that the irregular shape of the products and uncontrolled size particles were the main factors responsible for the catheter obstructions during embolization, these factors increasing considerably the risks of a surgical intervention. In the present invention, the produced particles have regular morphology and, therefore, allowing the reduction of risks associated to the embolization process.

Laurent et al. (1996) produced spherical particles with controlled morphology for embolization use. The particles, however, were formed with nuclei of trisacryl gelatin and shells formed by reaction of this gelatin with glutaraldehyde. In the present invention, PVAc forms the spherical particle nucleus and the shell is formed by PVA.

Beaujeux et al. (1996) observed that the use of spherical particles with controlled morphology enhances significantly the embolization performance, not only with respect to the reduction of catheter occlusions, but also with respect to the patient response to the treatment. They used, however, trisacryl gelatin particles in the study.

Lyoo et al. (1998) produced a high molecular weight PVA from the classical route of saponification in caustic methanol, using PVAc produced in suspension and in mass. It was used the azo compound ADMVN to effectuate the polymerization reaction at low temperature (30° C.). In the present invention it is not proposed the PVAc solubilization in caustic methanol to effectuate the hydrolysis.

The U.S. Pat. No. 6,160,025 (Slaikeu et al., 2000) claims an embolization method from PVAc solutions partially hydrolyzed and posterior precipitation in blood. The present invention does not propose the use of PVAc solutions to embolization, once the particles are already pre-formed.

Bendszus (2000) compared the embolization clinical performance conducted with trisacryl gelatin particles with controlled morphology, with commercial PVA of irregular morphology and came to conclusion that the clinical performances observed were similar.

The U.S. Pat. No. 6,191,193 (Kim et al., 2001) claims a process for spherical particles preparation of PVA/PVAc, with shell and nuclei structure, to posterior use as embolization agent. However, the process is based in the preliminary separation of PVAc particles produced in suspension by size range and posterior re-suspension of each size range for caustic treatment. Thus, the process of particles production is significantly more complex then the one here reported. Besides, the patent requires the use of methanol in the saponification medium and it does not report the clinical use of the particles produced for vascular embolization.

Mah et al. (2001) studied the PVA production from the classical process of PVAc saponification in caustic methanol, using, the VAc polymerization in emulsion started by a luminous source to produce the PVAc. They observed that the presence of oxygen might interfere in the reaction, obtaining products with lower molecular weight. In the present invention it is not proposed the PVAc solubilization in caustic methanol to effectuate the hydrolysis. Besides, the PVAc is produced in suspension.

Lyoo and Lee (2002) propose a PVA preparation method in a single batch, from VAc polymerization in suspension. The technique consists in addition of caustic methanol mixtures to the reaction medium after polymerization and conduction of saponification for two (02) days. The present invention does not require the use of caustic methanol and is capable of producing particles with shell-and-nuclei morphology with a saponification time much lower, in hour scale.

Wan et al. (2003) prepared PVA porous particles from cross-reactions initialized by epichloridrine in aqueous solutions and in inverse suspensions in paraffin. In the present invention it is not used reticulation agents, nor inverse suspensions of PVA aqueous solutions in paraffin.

In the U.S. Pat. No. 6,531,111 (Whalen et al., 2003) is claimed a polymer solution constitute for a biocompatible polymer, biocompatible solvent and contrast, in which the polymer precipitates to form particles used in embolization. The present invention does not presuppose the formation of PVA solutions to posterior precipitation.

The U.S. Pat. No. 6,627,600 (Boutignon, 2003) claims the use of PVA particles to impregnate medicaments and use for controlled liberation. In the present invention, the particles have a shell-and-nuclei structure, with PVAc nuclei and PVA shell.

Its important observe that the PVA particles commercially available and produced by saponification conventional processes in caustic methanol present the following disadvantages:

"Flocculated" aspect, as illustrated in FIG. 1;
Highly irregular surface, as illustrated in FIG. 1;
Ease of agglutination and aggregation;
Difficulty of passing through the angiographic catheter due to the irregular morphology illustrated in FIG. 1;
Susceptibility to degradation (biodegradation);
Future rechanneling of the treated vascular bed;
Costs too high.

The poly (vinyl alcohol) is obtained after poly (vinyl acetate) saponification. Due to the vinyl alcohol monomer tautomerism, one does not get to produce PVA by direct polymerization. The vinyl acetate polymerization can be effectuated in different ways. In the present invention, the vinyl acetate polymerization is effectuated in suspension, a process where the monomer, which is relatively insoluble in water, stays disperse in drops in a medium that has an initiator and a stabilizing agent. This agent stops the drops coalescence and dispersion during polymerization, reducing the interfacial tension and forming a superficial layer around the drop. In such a manner, the partially formed particles agglomeration is avoided and the particle spherical shape is preserved (Wood et al., 1997). The polymerization occurs in the monomeric phase and in most cases occurs by the way of a free radical mechanism. To avoid decantation and foam, agitation is used during the entire reaction. The type and velocity of the agitator employed, the dimensions and reactor geometry, the volumetric fraction of the monomeric phase and the type and concentration of the suspension agent employed influence the particles size distribution. The particle morphology is an important characteristic for the product formed application. Generally, in the polymerization in suspension the formed particles possess a pearl shape, with diameters in the range of 5-1000 μm (Dowding and Vicent, 2000).

In the saponification occurs the substitution of the acetate group for the hydroxyl group. It is used to this end solutions of strong acids or bases, generally sodium hydroxide (NaOH) solutions. The PVAc particle stays disperse in an aqueous medium under agitation, until the base addition and the reaction initialization.

After saponification the formed product possess a hydrolysis degree, also known as saponification degree, which represents the number of hydroxyl groups present in the molecule. A manner to determine the hydrolysis degree of formed PVA is from the ratio of methyl and methylene protons peaks of the hydrogen spectrum of NMR (Nuclear Magnetic Resonance). The PVA that presents a hydrolysis degree of about 81% possess a particular interest: it is the material that possesses the major solubility in water (Sandler et al., 1998).

The PVA possess varied utilization. Among them is of note its use as adhesives, as agents of suspension in polymerization, as agent for vascular embolization and as a film for instantaneous liberation cover in pills. Such a huge variety of application is owned to properties as the biocompatibility, the biodegradability, the good elasticity, the compressibility, among others (Marten, 1989). Due to these properties, the PVA is a strong appealing material for use in embolization procedures. However, the commercial sold products are presented as foam, not having a defined shape (Lacthaw and Gold, 1979).

With the present invention it is proposed viable routs of PVA/PVAc particles synthesis with shell-and-nuclei controlled morphology, aiming its application in vascular embolization. Classical polymerization procedures of vinyl acetate in hot and cold suspension are considered, followed by non-conventional hydrolysis via aqueous basic solutions and final steps of particles superficial treatment and purification promoted by radiation.

DETAILED DESCRIPTION OF THE INVENTION

The present invention describes the spherical particles synthesis of PVA/PVAc, obeying the procedures described in the following.

Choice of Materials

In the polymerization step vinyl acetate was used as monomer (Rhodia, polymer degree), distilled water as a suspension medium, benzoyl peroxide as initiator (Vetec), poly (vinyl alcohol) (Vetec) as agent of suspension and tertiary butanol as solvent. In the saponification step poly (vinyl acetate) new prepared and sodium hydroxide (Reagan) as caustic agent. In the particles superficial treatment step natural gelatin was used. None of the compounds was previously purified, with exception of water.

Its important observe that mixtures of vinyl acetate and others vinylic monomers, as acrylic acid and its derivatives, methacrylic acid and its derivatives, styrene and its derivatives, among others, in varied compositions in the range from 0 to 100% of vinyl acetate, may be used in the polymerization step. In such a manner, the use of pure vinyl acetate in the polymerization step in the examples does not limit the scope of the present invention. However, the reagent mixture must contain necessarily the vinyl acetate monomer, making possible to effectuate the caustic hydrolysis to vinyl alcohol during saponification. The use of pure vinyl acetate in the examples can be related to the fact that this compound is well tolerated by live organisms, on the contrary of others vinylic compounds. In this manner, the need of purification steps of the end product to remove the monomer residues is reduced.

Any other soluble initiators in vinyl acetate and capable of generating free radicals under thermal action, luminous or radioactive, as other peroxides and azo compounds, among others, and mixtures of these initiators can be used in the polymerization step. In this manner, the need of purification steps of the end product to remove the initiator residues is reduced.

In a similar manner, any other suspension agents, as hydroxy cellulose derivatives, aliphatic organic compounds salts, polar polymers (as acrylic poly-acid and sulfonated polystyrene), among others, and mixtures of these suspension agents can be used to prevent the suspended particles coagulation in aqueous medium. In this manner, the use of poly (vinyl alcohol) as a suspension agent does not limit the scope of this invention. Due to the fact that poly (vinyl alcohol) is used in the examples, this compound is accepted in a large range of medical applications and is well tolerated by living organisms. Besides, as the PVA/PVAc final particles have PVA shell, the use o PVA as suspension agent allows the process simplification and eliminates additional steps of particles purification with the objective of removing of suspension agents' residues.

Others organic solvents, as aliphatic hydrocarbons, cycloalkanes, alcohols, ethers, aldehydes, esters, among others, once they are at least partially water insoluble, can be used as solvent in the polymerization step. Therefore, the use of tertiary butanol as solvent in the polymerization step does not limit the scope of the present invention. The use of tertiary butanol in the examples is due to the fact that this compound is miscible with vinyl acetate, poly (vinyl acetate), poly (vinyl alcohol), benzoyl peroxide and is water insoluble. Besides, the tertiary butanol is an awful agent of chain transfer and allows obtaining polymers of high molecular weight in solution.

Other strong bases can be also used in the caustic treatment step, since they are soluble in water. In this manner, can be used strong bases or mixtures of metal strong bases, which characterize the groups IA and IIA of Periodic Table. The use o NaOH as a caustic agent does not limit the scope oh this invention. The use of NaOH in the examples is due to the fact that the sodium chloride (NaCl) is the saline compound present in bigger amount in the living tissues, what permits a considerable simplification of the purification process and to remove the final particulate material residues.

Other proteic materials, as lysozime and albumin, or polar polymers, as hydroxy-cellulose and its derivatives and the acrylic acid and vinyl alcohol polymers and copolymers can de used to the PVA/PVAc final superficial treatment, in such a manner that the gelatin does not limit the scope of the present invention. The use of natural gelatin in the examples is due to the fact that this compound is accepted in an enormous variety of medical applications and is well tolerated by the living organisms.

It was always observed that the state of the water is extremely important to the process. The presence of chloro ions in the commercial available water can result in the reaction inhibition and final product yellowish.

Therefore, the water utilized in the process must at least be distilled. The use of distilled water has been showed efficient in all cases.

Polymerization in Suspension

The polymerizations were conducted in a 1 l reactor, sleeved (FGG), whether or not in presence of ultra-violet radiation emitted by mercury lamp. The procedure consisted in addition primarily of a specified volume of an aqueous solution of the specified agent of suspension (in the range from 0 to 2 g/l, preferably equal to 0.7 g/l) until the medium temperature reached the desired value (in the range from 25° C. to 90° C., preferably 70° C.). Then it was added a monomer solution and solvent (in the range from 10 to 50% in mass related to total mass of suspension, preferably equal to 30%, having solvent in the range from 0 to 50% in weight, preferably equal to 0%), having also the initiator (in concentration in the range from 0 to 50 g/l, preferably equal to 10 g/l). The system was then maintained to a constant temperature under continuos agitation (in the range from 200 to 5000 rpm, preferably equal to 1000 rpm), for a pre-determined time (in the range from 0 to 12 hours, preferably equal to 3 h), before the saponification was initiated. The VAC/PVAc suspension was then submitted to caustic treatment in situ for a pre-determined time (in the range from 0 to 12 hours, preferably equal to 5 h). In an alternative way, the poly (vinyl acetate) formed was filtrated and washed abundantly with water, to realization of saponification in a second step of the process.

The experimental unit utilized to conduct the polymerization reaction; the saponification and surface treatment is showed in FIG. 3. The unit is constituted by the following apparatuses: (A) sleeved reactor, (B) thermocouple, (C) heating bath with programmed temperature, (D) tachometer, (E) impeller, (F) straight agitator constituted with 6 blades, (G) nitrogen bubble, and (H) reflux condensator. All equipments were sealed using teflon, in such a way to avoid leaking and contamination.

It is important observe that the equipment dimensions utilized do not limit the scope of the present invention. The 1-liter reactor use in the examples is due to the production of small amount of material, used in the laboratories studies. In the same manner, the geometry and the material used in the reactor construction do not limit the scope of the present invention, once the steel reactors and other materials can be used, having or not internal chicanes, serpentines cooling, distinct agitation blades, etc.

The use of a ultra-violet source light to induce the formation of free radicals does not limit the scope of the present invention. The use of luminous and/or radioactive radiation during the polymerization process allows to reduce the operation temperature and simultaneously increase the velocity of the reaction and modify the final polymeric material properties, in particular the molecular weight distribution. The use of luminous radiation allows also the utilization of photosensitive initiators and to reduce the need of an initiator amount to conduct the reaction, what, is advantageous in terms of final content of initiator residues in the final product.

The concentrations of suspension agent in the aqueous phase, the velocities of agitation utilized and the relative feeds of organic phase and aqueous phase do not limit the scope of the present invention. These variables allow the manipulation of particles final granulometry produced (bigger particles to smaller amounts of agents of suspension, smaller agitation velocities and bigger relative amounts of organic phase) e maintenance of suspension stability. The minimum agent of suspension content and maximum of organic feed depend on the agitation system geometry and the reactor refrigeration system (Machado, 2000).

Tem temperatures, initiator concentrations and solvent do not limit the scope of the present invention. These variables can be manipulated to vary the molecular properties of the end product and the velocity of reaction. Higher molecular weights and higher ramification degree are obtained with more high temperatures, more low initiator concentrations and more low solvent concentrations. The solvent concentration is used to manipulate the particle final density. Lower apparent densities are obtained with higher solvent concentrations.

The operational methodology defined to the examples presentation does not limit the scope of the present invention. The materials can be added in different ways, mixed or not with the others reaction constituents, in the beginning of (batch) or during (semi-batch) the polymerization procedure. The mixture of the agent of suspension in water and the mixture of solvent and the initiator in the monomeric solution allow obtaining much high homogeneity of the reaction system, but the reagents could be added in other manners. In a similar way, the aqueous phase addition primarily and the monomeric phase later, both in the beginning of reaction, allow obtaining a more stable suspension, given that the continuos phase is the aqueous phase. However, the addition can be also done in a inverse manner and during the polymerization. The temperatures and agitation velocities are kept constant in the examples, but can also be varied without limitations of the scope of the present invention. As shown by Machado (2000), increasing reaction temperatures, allow reducing the amount of residual monomer, while the velocity manipulation of agitation allows to modify the granulometric distribution of the end product.

Saponification

In the specified moment, a defined volume (equivalent from 0 to 200% of the aqueous phase initial volume, preferably equal to 100%) of caustic solution (with concentration from 10 to 60% in mass of strong base, preferably equal to 40%) was added to the reaction medium. The system was then left under continuous agitation (200 to 5000 rpm, preferably equal to 1000 rpm) in a specified temperature (in the range from 20 to 50° C., preferably equal to 30° C.) for a determined time (in the range from 0 to 12 hours, preferably equal to 5 h). The final particles of PVA/PVAc, with shell-and-nucleus morphology, were washed abundantly with water to remove residues and purification of the end product. The product was then filtered under vacuum and maintained in ambient free of humidity.

The possibility of realization of saponification in situ in the reaction ambient is one of the innovative aspects of the present invention. The volumes and concentrations of caustic solution, however, do not limit the scope of the present invention. These variables are utilized to define the process velocity of saponification and the final content of PVA in the particle.

In a similar manner, the range of agitation velocities does not limit the scope of the present invention, given that this variable serves only to maintain the system in suspension, avoiding the particle deposition at the bottom of reaction vessel.

The range of temperatures used is an important technological factor of the process. Low temperatures limit the saponification velocity and require the use of very long time caustic treatment. The use of high temperatures, however, promotes the yellowish of the material, probably because of the occurrence of caustic degradations lateral reactions.

Superficial Treatment

The produced particles can or not be re-suspended in an aqueous solution having one or more organic compounds partially soluble in water, as described previously, and been kept under constants agitation (50 to 5000 rpm, preferably equal to 1000 rpm) and temperature (in the range from 0 to 50° C., preferably equal to 25° C.) for a determined time (in the range of 0 to 12 hours, preferably equal to 1 hour). The organic material is distributed on the new-formed particles surface and modifies the hydrophilic/hydrophobic character of the surface, allowing the modification of the interaction of the particles with the walls of the surgical catheter (which can be made of different materials).

The use of the particle final superficial treatment constitutes an important technological advance to practical use in surgical interventions. The superficial treatment allows that the particle interacts in an appropriate manner with the surgical catheter, avoiding agglomeration and catheter clogging during the intervention.

Sterilization

Dry sterilization tests were performed (sterilization by γ-rays) and by humid via (sterilization of aqueous suspension in autoclaves at 120° C.). The tests consisted in the sterilization of the PVA produced and in the following stability verification of the produced material, using the analysis techniques of XRD, DSC and optical microscopy.

In the realization of the dry tests were utilized γ-rays emitted by a Co-60 canon. The sterilization was done in small glass flasks containing around 100 mg of dry sample.

The samples were submitted to γ radiation for an 18 hours time with intensity of 25 Kgray. The sterilized material, after characterization, presented always the same properties of the original material, indicating that the dry sterilization does not alter the produced material properties in the evaluated conditions and can be used with confidence to preparation of clinical samples.

To the realization of humid sterilization tests, aqueous suspension were prepared containing 10% of PVA, that were maintained in glass flasks under agitation during 1 hour and temperatures up to 120° C. The sterilized material, after characterization, presented always the same properties of the original material, indicating that the sterilization by humid via does not alter the produced material properties in the evaluated conditions and can be used with confidence to preparation of clinical samples.

For the reasons described before, no more additional mentions are made to the sterilization process in this document. It's important to observe that the specific conditions of sterilization do not limit the scope of the present invention. The sterilization step can be conducted by other manners; however, in the sterilization conditions here presented, is guaranteed that the material properties are kept stables.

Analysis Sample Preparations

The analyzed samples were prepared according to the established needs in each technique. In the preparation of the sample taken to XRD (x-ray diffractometry, in a Rigaku dmax 2200 diffractometer, Rigaku/MSC, using CuK radiation), the material was previously sieved and in the following fixed in a small metallic plate. In the sample preparation to DSC (differential scanning calorimetry, in DSC7 calorimeter, Perkin-Elmer, at heating rates of 10° C./min), 10 mg of the finely divided material, in the range from 50-150 μm, was weighted, in an analytical balance and added to a metallic little pan. In the sample preparation to NMR (proton nuclear magnetic resonance, $^1$H-NMR, and of carbon, $^{13}$C-NMR, in a Varian Mercury 300 spectrometer, Varian Instruments, operating at 100 MHz and equipped with probes of 10 mm), about 10 mg of the material were added to 5 mL of deutered DMSO (dimethyl sulfoxide), in the following being submitted to the ambient temperature analysis. In the GPC preparation (Gel Permeation Chromatography, Waters 600E Chromatograph, equipped with Phenomenex™ linear columns with porosity in the range from $10^3$ to $10^6$ A, with a SFD refraction index detector RI-2000F, Schambeck, with Konic high precision pumps, calibrated with polystyrene standards supplied by the manufacturer), about 15 mg of the sample were dissolved in 8 mL of THF (tetrahydrofuran) and analyzed with 200 μL injections at 40° C.

Characteristics of the Obtained Material

The polymerization reaction of vinyl acetate results in a product with spherical shape and size in the range from 50 to 500 μm, which granulometric distribution depends on the operational conditions, as described previously. The FIG. 2 illustrates the produced material morphology. The XRD analysis indicates the formation of different particles as illustrated in FIG. 4. It is observed the formation of pure PVAc, PVA/PVAc and pure PVA particles depending on the saponification condition. The DSC analysis, illustrated by FIG. 5, also indicate the formation of different particles, depending on the operational conditions. The presence of PVA can be illustrated by displacement of the end product vitreous transition temperature. The FIG. 6 shows RMN spectrum, where are detected the typical peaks of the PVA and PVAc, as discussed by Nozakura et al. (1976). However, the differences between the spectrums are weak in the analyzed region, turning the quantification difficult. The FIG. 7 shows the GPCs of the produced materials in different conditions. It's clear that the operational conditions can be conveniently manipulated to alter the molecular weight distribution of the end product.

Experimental Study In Vivo of the Inflammatory Reaction Between Commercial PVA (Imported) and the Shell-Nuclei Spherical Pva+PVAc The embolization is a procedure well established to the treatment of many vascular lesions. The PVA is one of the biocompatible embolic agents most utilized. However, the commercial product presents irregular morphology, facilitating the aggregation and making difficult its practical use. The objective of this example is the evaluation in vivo of the characteristics and the effects caused by the use of PVA particles available commercially, and making a comparison with the effects caused by the use of PVA/PVAc spherical particles described before, after intra-arterial embolization in kidneys of albino rabbits of the type New Zealand. The experimental results show that both particles are effective to cause tissue isquemia. However, the inflammatory reaction is more intense as desired when the particles described by this invention are used, which also promote a higher penetration degree in the vascular system.

Material and Method

The Ethical Commission in Research for Animals (E.C.R.A) of the UFRJ Surgery Department approved this study. New Zealand albino rabbit females were used, weighting between 2.300 g and 3.200 g, that were submitted to renal intra-arterial embolization, under intra-muscular amnesty, divided in two groups of 24 animals. The rabbits of one group were submitted to embolization with commercial PVA (Trufill™, Cordis, Miami, Fla., USA). The other group of rabbits was submitted to embolization with spherical PVA+PVAc (object of this invention), produced in the Example 2). Both groups were subdivided in four subgroups of six animals (n=6), kept in captivity until euthanasia for post-operatory periods of 48 hours (see FIG. 8), 5 days, 10 days and 30 days (see FIG. 9), respectively (Table 1). Also was effectuate an additional group of simulation (sham), divided in four subgroups of three animals (n=03), kept until euthanasia for equal period of time as the groups submitted to embolization (Table 1).

TABLE 1

| Simulation Group (SHAM n = 12) | | Commercial PVA Group (n = 24) | | Spherical PVA + PVAc Group (n = 24) | |
|---|---|---|---|---|---|
| Subgroup | (n) | Subgroup | (n) | Subgroup | (n) |
| 48 hours: | (n = 03) | 48 hours: | (n = 06) | 48 hours: | (n = 06) |
| 5 days: | (n = 03) | 5 days: | (n = 06) | 5 days: | (n = 06) |
| 10 days: | (n = 03) | 10 days: | (n = 06) | 10 days: | (n = 06) |
| 30 days: | (n = 03) | 30 days: | (n = 06) | 30 days: | (n = 06) |

In euthanasia, were taken off the kidneys submitted to embolization and the contra-laterals, used as control, and send to anatomopathologic analysis for posterior comparative study.

Amnesty, Preparation of Guinea Pig and Surgery Technique

Ketamine chlorohydrate (Vetanarcol™, König) was utilized, in a dose of 40 mg/kg and xylazine in a dose of 2 mg/kg, via intra-muscular. Also, lidocaine chlorohydrate 1% was utilized in the incision place.

The animal was placed in dorsal decubitus, with the four members contained. Tricotomy of the right inguinal region was effectuated, with posterior skin assepsy and anti-assepsy, with iodide solution and sterilized operatory fields were placed in position. Inguinal surgery access was effectuated, with identification and repair of the right femoral artery. Heparinization was full in the dose 100 UI/kg, via intra-arterial.

The fluoroscopic and angiographic study was carried out with "C" arc, unity of mobile fluoroscopy, BV-300 (Philips, Holland). Introduced angiographic catheter of polystyrene (DAV™, Cook, Bloomington, Ind., USA) of 4.1 French (Fr.), leaned on hydrophilic guide wire (Roadrunner™, Cook, Bloomington, Ind., USA). After that a selective chaterism was performed with the right renal artery, under fluoroscopy, with injection of iodide contrast (Reliev™, Justesa) to obtain the renal angiographic study pre-procedure with evaluation of the arterial phases, parenquimatosis and venous return. After that, intra-arterial embolization was carried out with commercial PVA or spherical PVA+PVAc particles, with diameter from 150 to 250 μm, suspended in 20 ml of physiological salt solution a 0.9%, according with the body weight of the animals (Table 2).

TABLE 2

| Body Weight | Dose |
|---|---|
| 2.300 g to 2.600 g | 15.0 mg |
| 2.600 g to 2.900 g | 17.5 mg |
| 2.900 g to 3.200 g | 20.0 mg |

A posteriori an angiographic control study was carried out to evaluate the effect of the procedure on the kidney vascularization. After the angiographic catheter was taken off, it was effectuated a proximal and distal suture of the femoral artery. Homeostasis revision and skin close with continuous suture, with monofilament wire 4-0 (Mononylon).

Sample Collecting and Histopathological Study

The animals were submitted to euthanasia with intravenous injection of thiopental and potassium chloride, in the marginal vein in the ear. Both kidneys were withdrawn (the embolized one and the contra lateral), with median laparotomy. The kidneys were sectioned longitudinally in the half (coronal direction), being immediately immerses and kept in a 10% formaldehyde solution.

The histopathologic study was performed trough the utilization of conventional optical microscopy. About of 3 mm fragments obtained from the embolized and contra-lateral kidneys, fixed in a 10% phormol, were dehydrated in increasing concentrations of ethyl alcohol, diaphaned in xylol and put in paraffin blocks. Cuts of 5 μm thick were effectuated, being submitted to coloring techniques, by the methods of hematoxiline-eosin (HE) and Masson's trichrome. The observation was performed in optical microscopy (Leitz-Dialux), in the HUCFF/UFRJ pathological anatomy service. After that, the images were digitized trough digital camera (Samsung), coupled to the optical microscopy.

Results

As the result of the surgical technique and embolization procedure, all kidneys were selectively catheterized without difficulties. Referring to the embolization procedure does not occur aggregation or agglutination during the particles flux, not only with the commercial PVA particles but also with the spherical-PVA+PVAc particles, trough the 4-F catheter. In the final control angiographic study, it was observed occlusion of renal circulation in all animals. Independent study carried out with the particles without the final superficial treatment resulted in agglomeration and in catheter clogging, indicating that the step of superficial treatment may have great practical importance in the particles production process, depend on the type of catheter used in the surgical intervention.

Results of the Macroscopy Study

In the kidneys, with 48 hours of embolization were noted the paleness of the subcapsular cortical surface and, when cut, discrete faint of the cortical-medullar limits, associated to light hyperemia of the medullar. Such alterations were accentuated proportionally in the kidneys with 5 and 10 days of embolization, with paleness also in the medullar, until the complete loss of the cortical-medullar limits, when compared with the contra-laterals kidneys utilized as controls. In the embolized kidneys with the spheres this aspect appeared less homogeneous, with areas chestnut-colored, mainly peri-hilares.

The kidneys with 30 days of embolization showed significant decreasing in volume, more accentuate in the animals submitted to embolization with the spheres. The kidneys embolized with commercial PVA had the external cortical surface and the cut surface with an aspect similar to the one observed with 10 days of embolization. However, in those embolized with PVA/PVAc spheres, the external cortical showed scar depressions and renal capsule thick and adhered; when cut were noted homogeneous areas of cartilaginous aspect and others yellow creeping.

Result of the Histopathologic Study

48 Hours Results:

in the microscopy study of the embolized kidneys for 48 hours, were observed the presence of commercial PVA and spherical PVA/PVAc particles in the interior of the vessels inter-sperse with red blood cells and sparse polymorphonuclear (PMN), both more numerous with commercial PVA. With this product, were noted ischemic alterations of the arterial wall with focal area of rupture and with afflux of polymorphonuclear, not observed in the embolized vessels with spherical PVA/PVAc.

With both particles were observed, in the cortex level and of medullar, important ischemic answer with nuclear pycnosis, karyorrhexis and karyolysis, beside of vacuolization and cytoplasmatic fragmentation in tubular and glomerular cells, associated with congestion. These alterations were visualized in the two groups of animals, but in the embolized with spherical particles were noted preserved areas corresponding to the chestnut-colored regions described in the macroscopy. In the subcapsular cortex there was yet inflammatory infiltrated in bandage, constituted with integer or degenerated polymorphonuclear.

5 Days Results:

In this step were observed in the kidneys of the commercial PVA particles, numerous polymorphonuclear and red blood cells among the particles, which were vacuolated. The vascular wall shows focal areas of permeation by PMN, related to cellular lyse. It is still observed in the subcapsular cortical region infiltration by PMN, accentuation of the cellular necrosis process and calcification points.

With the spherical PVA+PVAc particles were observed accentuate inflammatory infiltrate of subcapsular PMN, as also the permeation through these cells of the other areas of the organ, where the necrotic alterations appeared more accentuate than in the anterior period. Multiple calcification points are associated in the medullar, where still were observed accentuate congestion and regeneration of the cellular epithelium, together with interstitial granulation tissue. The spherical PVA+PVAc particles filled practically all the vascular lumen, inter-sperse with red blood cells or by thrombus in organization.

10 Days Results:

In this period, the embolized vessels with commercial PVA particles show wall necrosis, sometimes related to PMN; the particles being intensely vacuolated and retracted. To the cortical and medullar level, the ischemic alterations appeared prominent, with PMN organized in subcapsular bandage and occasional points of mononuclear (lymphocytes).

With the spherical PVA+PVAc particles were observed intense infiltrate of subcapsular PMN in bandage and around the particles presence of organized thrombus. In the cortical and medullar level were visible important ischemic alterations associated with congestion, with multiple calcification points, interstitial fibrose and regeneration of the tubular epithelium, especially in the medullar. Were noted some preserved areas inter-sperse with points of isquemia.

30 Days Results:

In the kidneys with commercial PVA particles were observed in 30 days important retraction of PVA particles, permeated by calcium deposits, with vascular wall becoming thin and fibrosis. In the cortical persist the ischemic alterations associated with the calcium deposition. In the coloring by Masson's method, were observed the presence of rare subcapsular, cortical and medullar fibrosis, where tubule with regenerated epithelium was noted.

In this step, the spherical PVA+PVAc particles appeared surrounded by organized thrombus; in, the vicinity of these vessels were noted focal accumulations of mononuclear inflammatory cells. It is of note the present calcification in the cortical and medullar regions associated to the presence of intense fibrosis. Were still found large areas of ischemic necrosis, epithelia of medullar tubule regenerated and small areas with still preserved parenchyma.

Discussion of Results

The rabbit was the chosen guinea pig for being an animal of small-scale and for presenting vascular anatomy similar to the human one. The kidney was chosen for being an organ with terminal vascularization and bilateral presentation, what make easy the comparative study between the kidney submitted to embolization and the kidney contra-lateral for control, not embolized, and yet allow to maintain the animal vital functions. It was chosen to standard the study using only female guinea pigs and effectuates the embolization exclusively with the right kidney, in a complete manner, in all guinea pigs.

The established date for the euthanasia were also standardized, in 2/5/10/30 days, based on the times of changing of the different phases of the inflammatory reaction, already established in previous microscopic heart studies, with myocardium stroke, once the purpose of this study is to study the inflammatory reaction that occurs in the kidney with renal stroke, promoted by complete occlusion of its vascularization with the two different kind of embolic agents studied.

The trans-catheter embolization procedure as treatment of a variety of medical conditions has been more and more used in the last years. The embolization technique consists in the injection of synthetic material after effectuate selective catheterism of the blood vessels that irrigate the compromised area in a manner to occlude mechanically the blood flux that feed the region to be treated. The intravascular embolization constitutes important strategy in tumors, aneurysms and vascular malformations fighting.

With the objective of outline the undesired characteristics inherent to PVA particles commercially available, different manners of use has been experienced and various new substances has been created and tested. Derdeyn et al. (1995) effectuated an study with the objective of evaluation the characteristics of commercial PVA particles and determine if it changes its size when suspended in medium of contrast non-ionic or when suspended in an alternative solution of contrast non-ionic and absolute alcohol, and concluded that the commercial PVA particle increased significantly its size in the two different solutions, once the commercial PVA is a polyvinyl foam that has a behavior as a sponge. Choe et al. (1997) effectuated a study to evaluate the embolic effects according to the infusion velocity and with the commercial PVA concentration in suspension, and concluded that more slow infusions of suspensions more diluted are capable of promoting arterial occlusion more distal, once that the commercial PVA particles are more disperse in solution and the chances of aggregation are lower.

The PVA for medical use was utilized for the first time in 1949, by Grindlay in an experimental study with the use of PVA sponge after pneumectomy, that during necropsy revealed that the PVA was inert and readily invaded by tissue fibrosis with a minimum amount of inflammatory cells. After this one, several other experimental studies were performed, such as the use of PVA as skin substitute that in 1960 decade begins to be used as a skin substitute in burnt patients. Besides, the use as coadjuvant in treatment of rectal prolapse or as a choice material in cardiac surgeries in closing defects of septo. In 1974, Tadavarthy presented the PVA as a possibly ideal transcatheter arterial embolization agent possibly ideal, in promoting complete occlusion of the vessel, permanent hemostasia and thrombosis. From this work on, the PVA particles started to be largely used and studied in several medical conditions.

The PVA particles initially used in the shape of foam or sponge also presented other inconvenient as difficult preparation and presentation with great variation in the particles size. The particles in initial presentations of only 250-590 or 590-1000 μm in diameter were still prepared in formalin and previously to embolization should be washed with sterile solution to eliminate any residue. In the following, they begin to be cut in pre-determined size and manoeuvers were created with intuit of avoiding particle aggregation, with the utilization of a mixer to keep them uniformly in suspension.

Initially, the commercial PVA particles were adopted as embolization agents in urgencies, as pos-trauma splenic bleeding and pos-birth womb hemorrhage, or as pre-operatory coadjuvant, in proportioning lower chances of bleeding during surgical act in womb myomas and intra-skull meningiomas. Nowadays, commercial PVA may be used as unique therapeutic method agent in treatment of womb leiomyomas, with symptomatologic improvement up to 95% of the patients and with myomatous mass retraction up to 73%, under ultrasound control. In 1995, Ravina perceiving that the womb leiomyoma of patients that were submitted to emergency embolization or pos-operatory presented mass retraction, published for the first time a work referring to embolization of womb arteries with primary treatment of women with myoma.

Believing that the irregular shape of commercial PVA particles is responsible by the aggregation and agglutination of themselves, a variety of embolic agents of spherical shape have been developed. The agents have been developed from different organic or inorganic materials, including collagen, dextran and trisacryl polymer impregnated with gelatin.

The PVA+PVAc spherical particles developed in this invention were observed experimentally and demonstrate to penetrate more in a distal way than the commercial PVA particles studied and can be injected with less difficulty.

The PVA+PVAc particles were observed uniformly spherical and with smooth surfaces in all the samples available and in the different produced diameters. It is not noted any small fragment. The commercial PVA particles generally present a flocculated irregular shape, with irregular and sharped angle projections. After suspension some small fragments have been observed.

The spherical PVA+PVAc particles presented easier flux through the catheter than the commercial PVA particles. Catheter agglomeration and occlusion was not observed with the spherical PVA+PVAc particles. These differences may be attributed to the smooth surface of the spherical PVA+PVAc particles.

Derdeyn et cols. (1997) in an experimental comparative study between the commercial PVA particles and the acrylic micro-spheres coated with collagen of the same size (Embosphere™, Guerbet Biomedical, Louvres, France) observed a significantly difference in the particles penetration degree. When the commercial PVA particles frequently aggregate in the ascendant pharyngeal artery of pigs, the micro-spheres particles reached and go beyond the microcirculation. These authors attributed this difference to the characteristics of micro-spheres particles, which present smooth and hydrophilic surface, can be deformed and do not aggregate. They refer yet that these characteristics are responsible by the easy of injection of micro-sphere particles and by the central non-accumulation and catheter occlusion. The penetration degree of the commercial PVA particles inside the vascular system can be affected by many factors. The announced size of a commercial PVA particle is primarily a function of its intermediate axis, which is responsible by the particle ability of passing through the sieve square holes responsible by particle separation of commercial PVA by sizes. When the vessel diameter is small to the particle intermediate diameter, it clogged in the vessel.

However, Quisling et al. (1984) showed that commercial PVA particles tend to adhere on the vessels walls of bigger diameter before they come to clog in a distal vessel. Besides, the commercial PVA particles tend to pile up and aggregate inside the catheter. Similar accumulations can occur inside the vessel in the place of particles adherence. The vessel occlusion with commercial PVA particles can occur for these reasons frequently in a place more proximal than the expect one for a given particle and a certain diameter of the vessel light.

Beaujeux and cols. (1996) noted that the micro-spherical particles should be utilized in sizes bigger than the predicted ones to occlude completely a vessel during an embolization. They attributed this need to the fact that the initial choice for a determined particle size was based on the experience of the medical group with the commercial PVA particles.

The higher degree of penetration observed with the spherical PVA+PVAc particles may be advantageous in effectuating a trans-arterial embolization more effective of many injuries. However, in injuries with evidence of communication artery-venous must be necessary more studies, once Derdeyn and cols. (1997) reported in study with micro-spherical particles that they can transpose the injury and promote pulmonary embolization. The higher penetration degree observed with the spherical PVA+PVAc particles can also be attributed to its compressibility capacity, adjusting to the vessel conformation, being able in this way to reach more distal vessels.

The commercial PVA particles promoted moderated inflammatory responses while the spherical PVA+PVAc particles promoted intense reaction, what can be due to the higher particle penetration degree, beyond of corresponding to the thrombus reactions and the occlusion of the proper vessel.

The spherical PVA+PVAc particles the same as the commercial PVA when do not promote occlusion, they do not promote any inflammatory reaction, i.e., they are inert. Being the inflammatory response only observed when the vessels are completely occluded.

The vessel occlusion promoted by the commercial PVA particles, being formerly considered permanent, it is known that it occurs once this particles are biodegradable and the vessel rechanneling occurs. The histopathological studies obtained in this study showed that the commercial PVA particles suffer a big retraction in the 30 days parts.

As the commercial PVA particles present a very irregular shape, allow the appearance of spaces among them that will be filled with blood, which consequently to the vessel occlusion turns into thrombus. What favours the vessel rechanneling by occurring the thrombus reabsorption with inflammatory reaction. Associated to this, the commercial PVA particles degradation will favour still more the vessel rechanneling.

In the parts examination in lamina were observed that the spherical PVA+PVAc particles presented better adaptation among themselves and the vessel, promoting in this manner the formation of less spaces to be filled by blood, being then, the amount of blood in the spaces in small quantity. Being reabsorbed it was not a sufficient factor to favour the vessel rechannelling.

The anatomopathological study still shows that the inflammatory reaction promoted with the vessel occlusion by the spherical PVA+PVAc particles occurred in more distal vessels and were more intense than with the commercial PVA particles, promoting cellular growth into the interior of the vessel light, with consequent fibrosis of it, making difficult in this manner any chance of rechannelling of this vessel.

Our results demonstrated that the spherical PVA+PVAc particle is an effective embolic agent, easy of passing through the catheter and does not agglutinate in the vessels, reaching more distal arterial segments than the commercially available PVA particles. According with the experimental results obtained, the spherical PVA+PVAc particles present physical, chemical and biological properties desirable to an embolization agent, being an attractive option for transcatheter intra-arterial embolizations.

Figure 1:
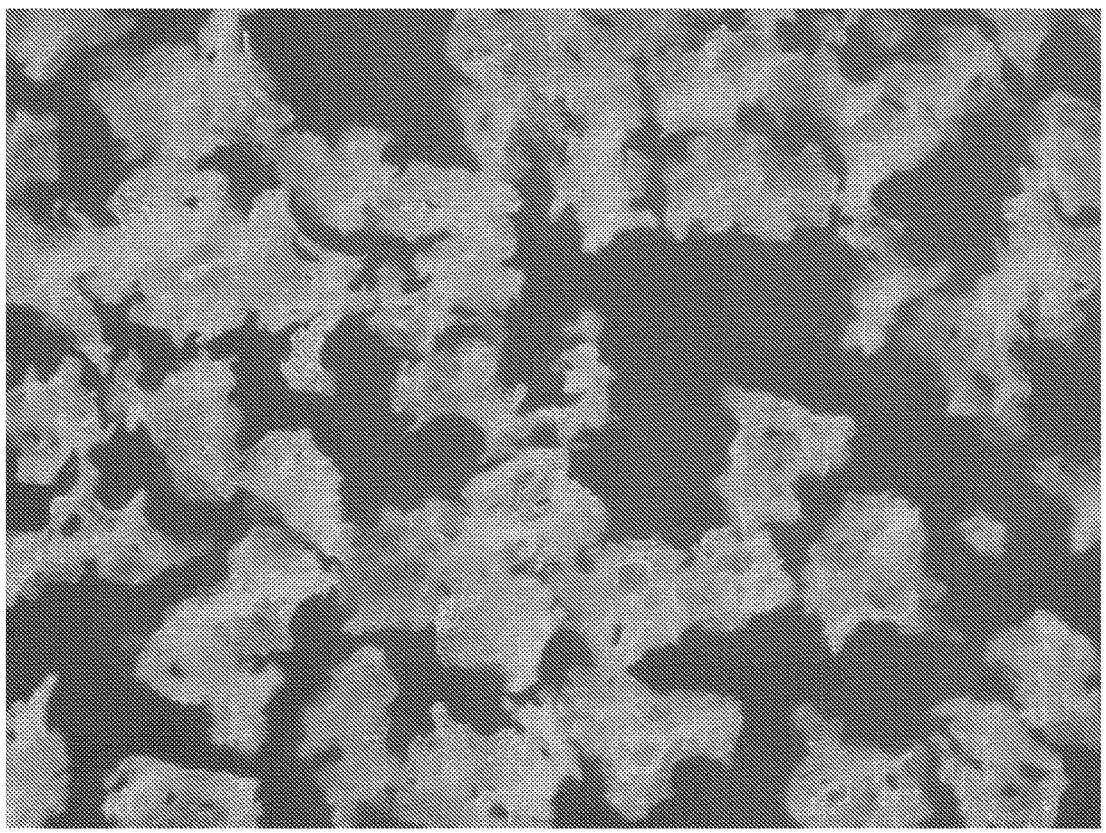
FIG. 1—PVA particles morphology produced by the traditional precipitation method from a solution.
Figure 2:
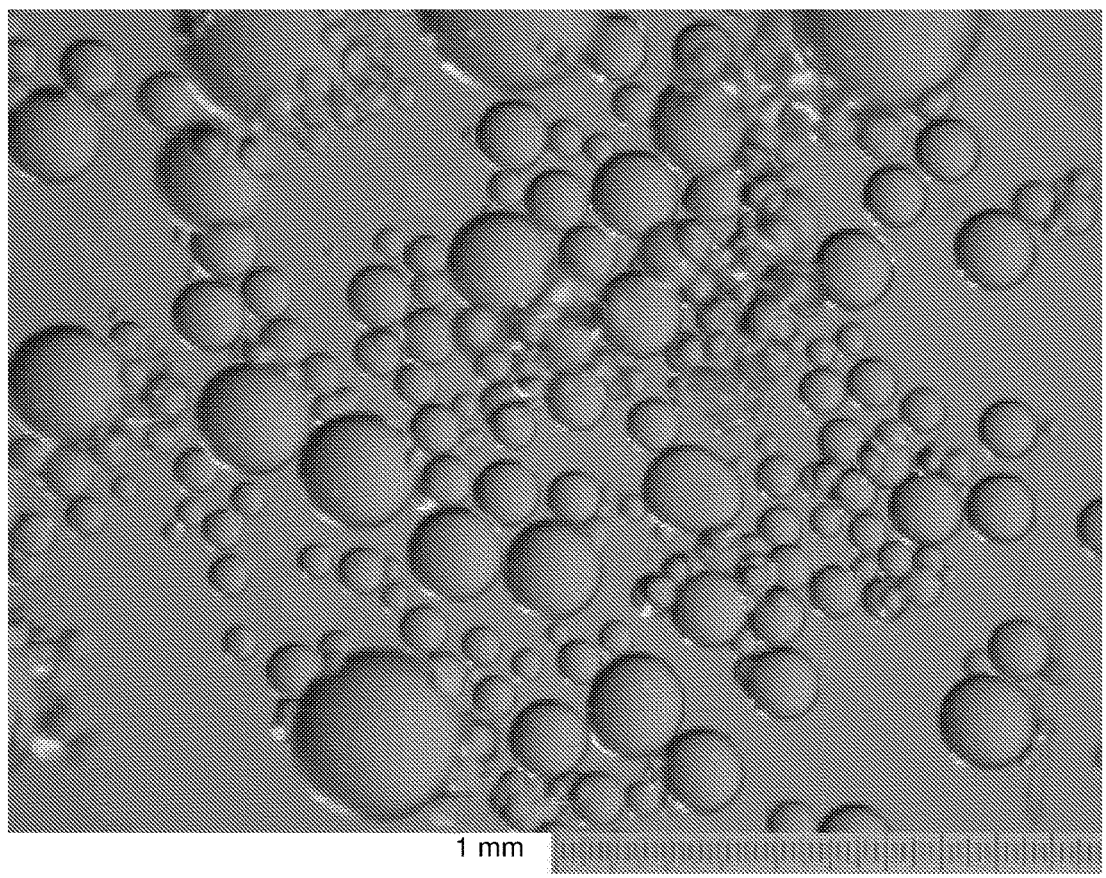
FIG. 2—PVA/PVAc particles morphology produced from the technique proposed in this patent.
Figure 3:
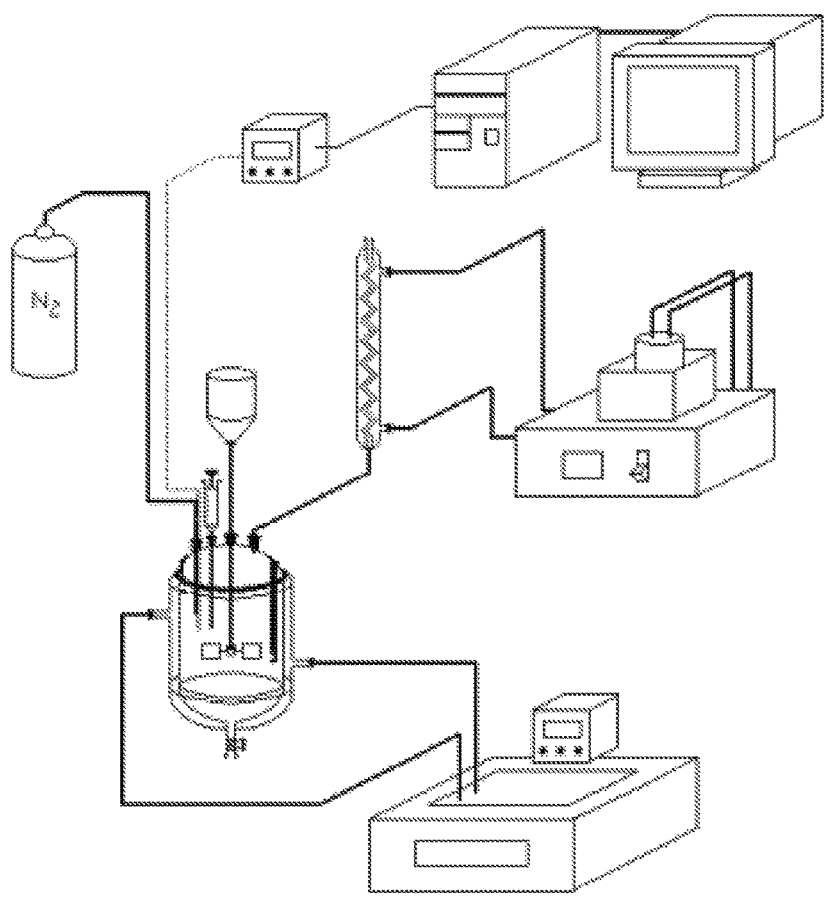
FIG. 3—Experimental unit.
Figure 4:
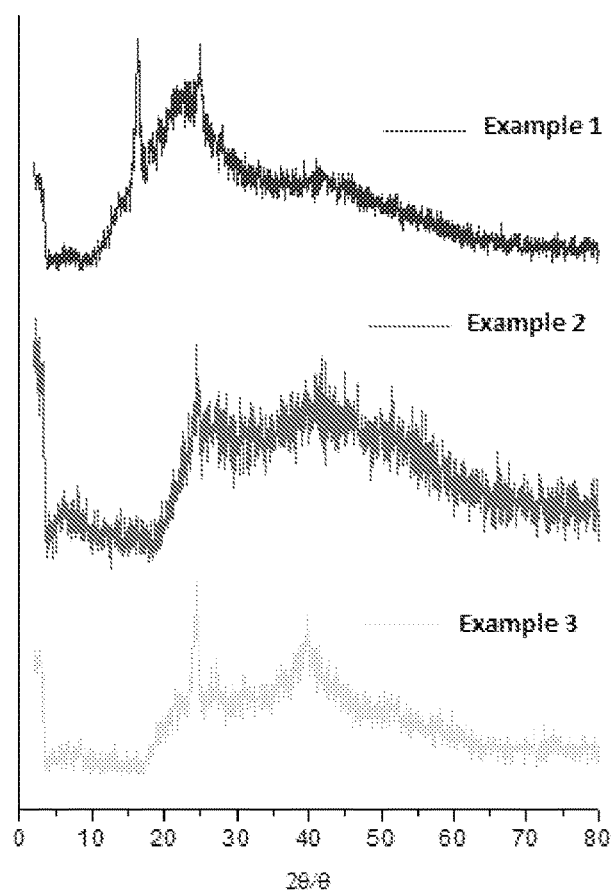
FIG. 4—XRD spectrum obtained for different products. (A) Non saponified material (Example 1); (B) Saponified material by 5 hours at 30° C. and 20% of soda in the aqueous phase (Example 2); (C) Saponified material by 24 hours at 30° C. and 20% of soda in the aqueous phase (Example 3).
Figure 5:
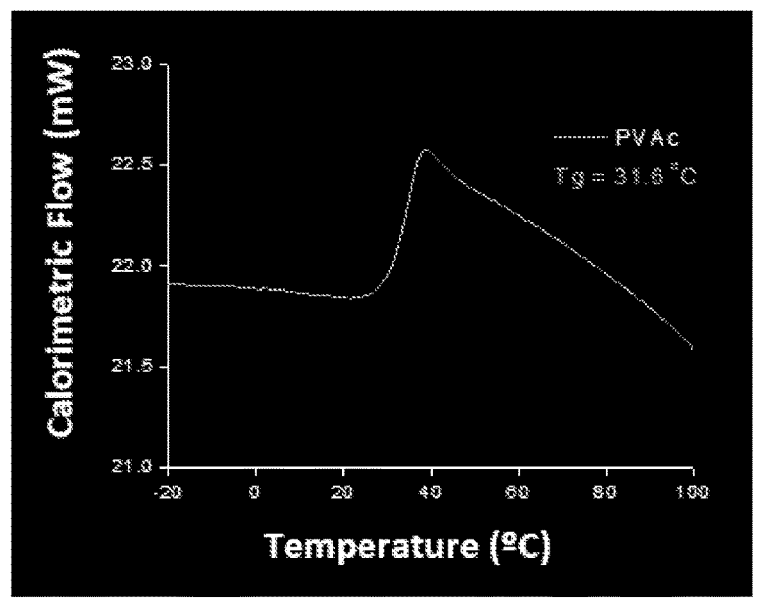
FIG. 5—DSC spectrum obtained for different products. (A) Non saponified material (Example 1); (B) Saponified material by 5 hours at 30° C. and 20% of soda in the aqueous phase (Example 2).
Figure 5:
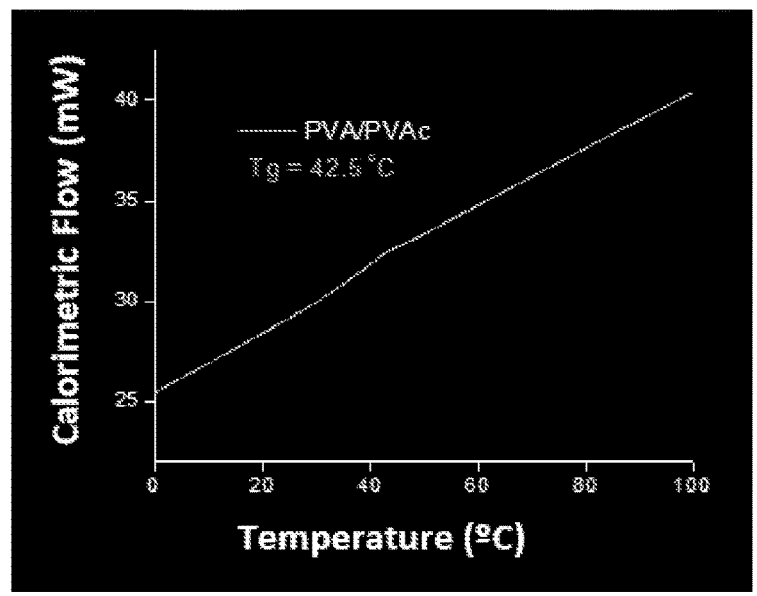
Figure 6A:
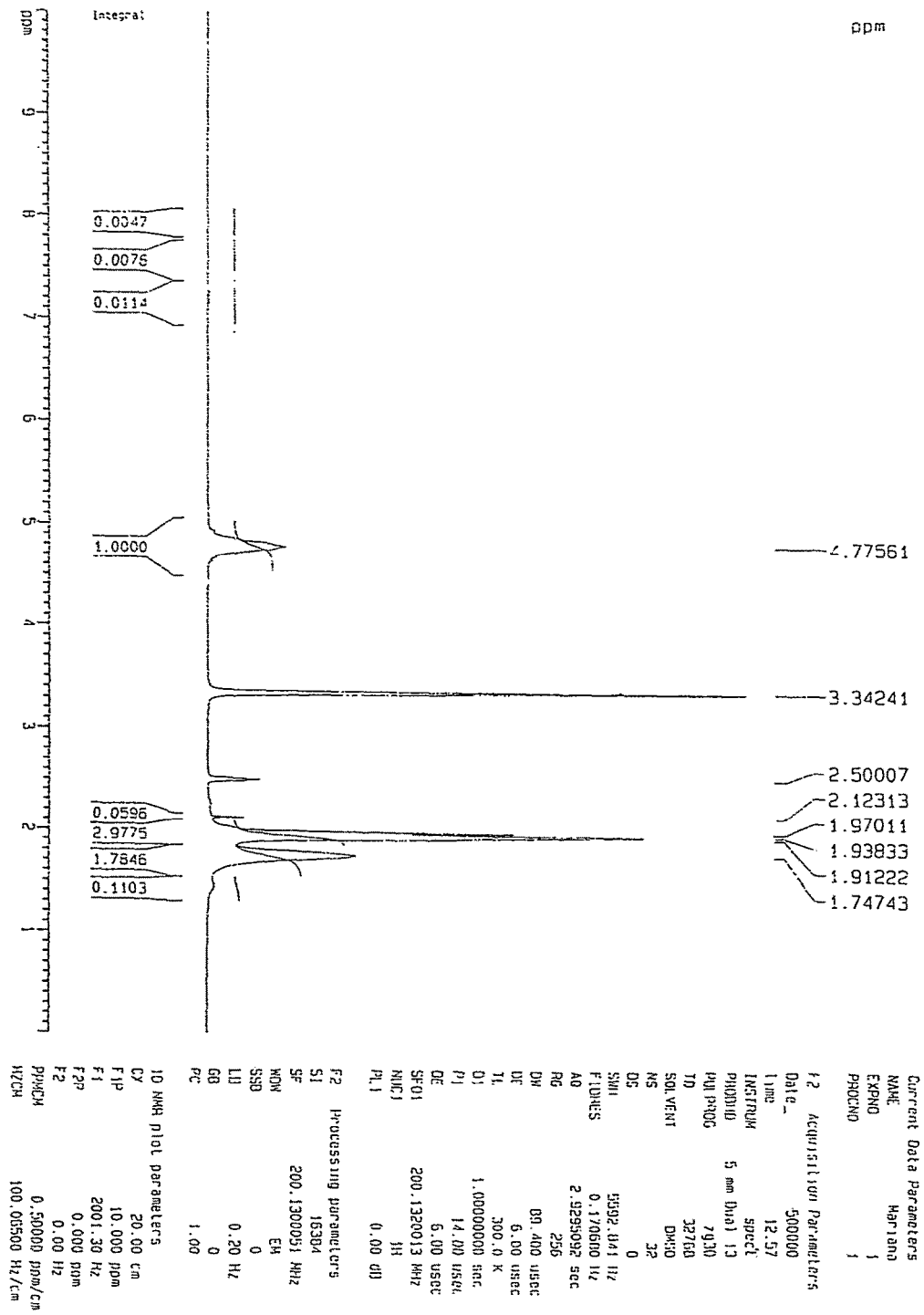
FIG. 6—RMN spectrum obtained for different products. (A) Non saponified material (Example 1); (B) Saponified, material by 5 hours at 30° C. and 20% of soda in the aqueous phase (Example 2).
Figure 6B:
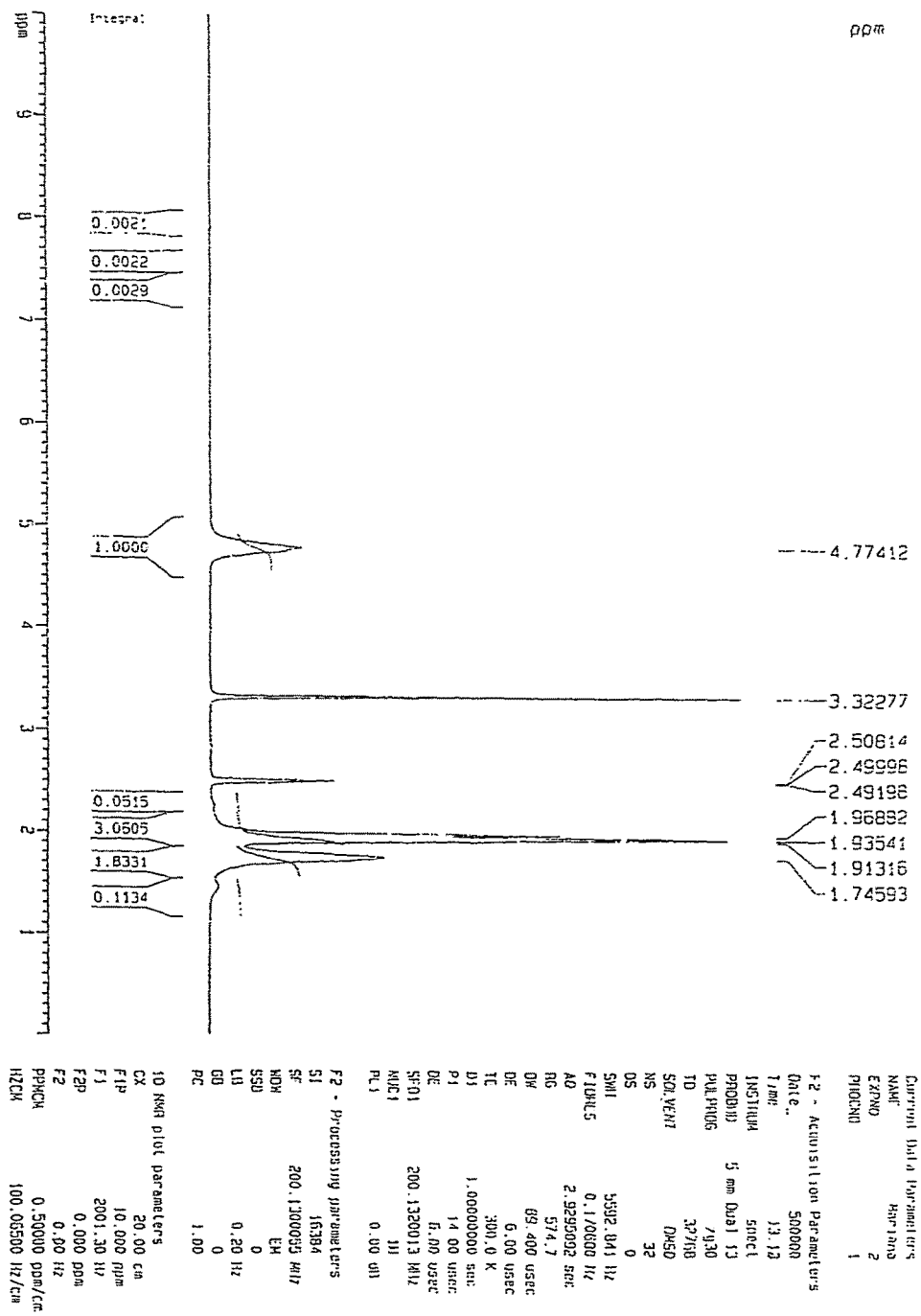
Figure 7A:
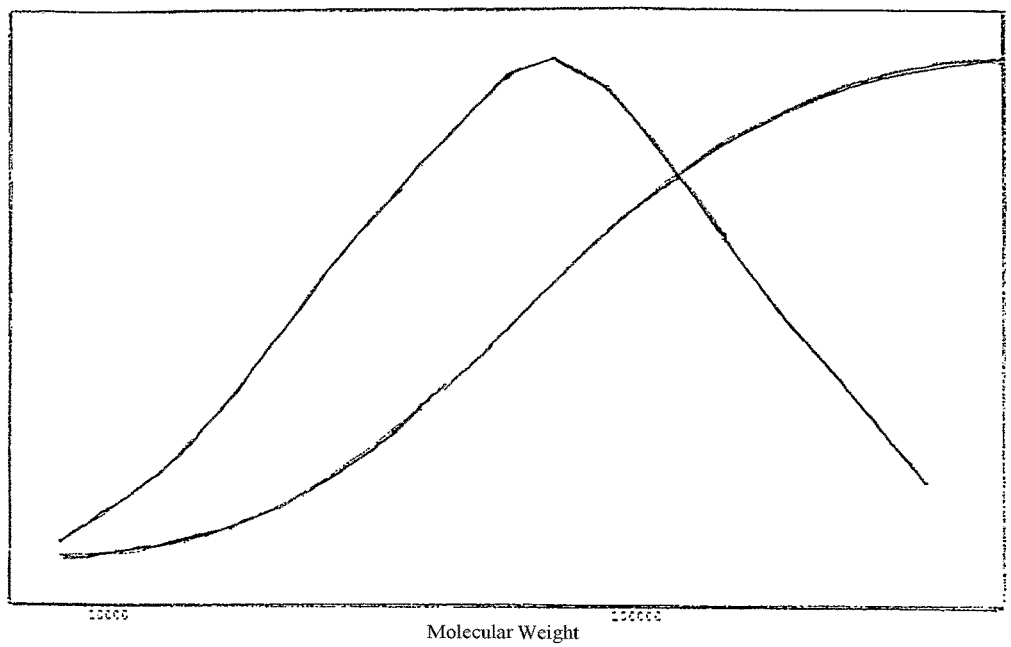
FIG. 7—GPC spectrum obtained for different products. (A) Material produced at 70° C. with initiator, without ultra-violet light and without solvent (Example 2); (B) Material produced at 300° C. with initiator, with ultra-violet light and without solvent (Example 4); (C) Material produced at 5000° C. without initiator, with ultra-violet light and without solvent (Example 5); (D) Material produced at 70° C. with initiator, without ultra-violet light and with 25% of solvent (Example 6); (E) Material produced at 70° C. with initiator, without ultra-violet light and without solvent, with surface treatment (Example 7).
Figure 7B:
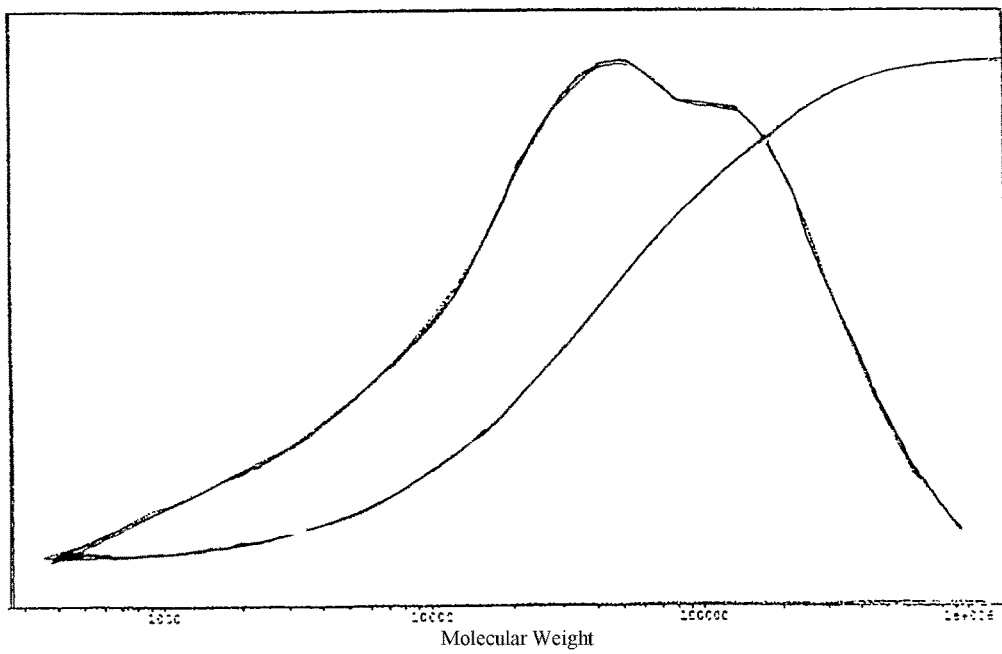
Figure 7C:
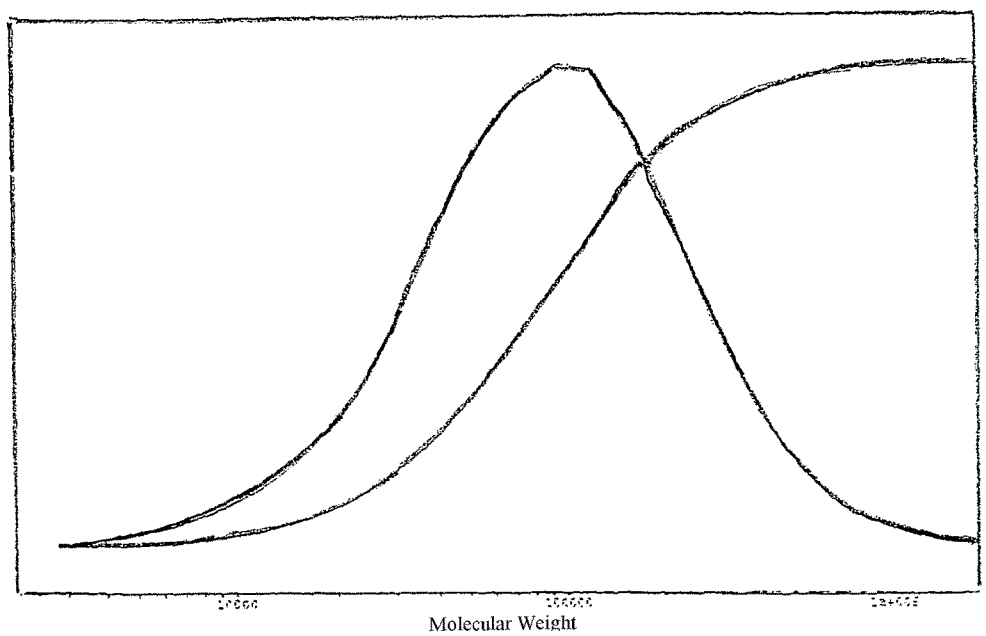
Figure 7D:
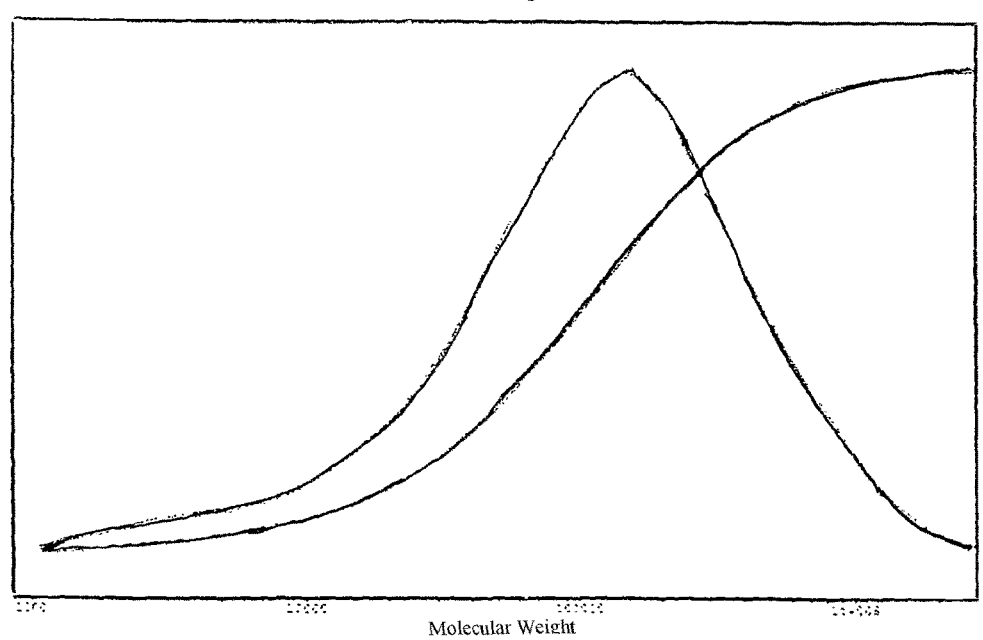
Figure 7E:
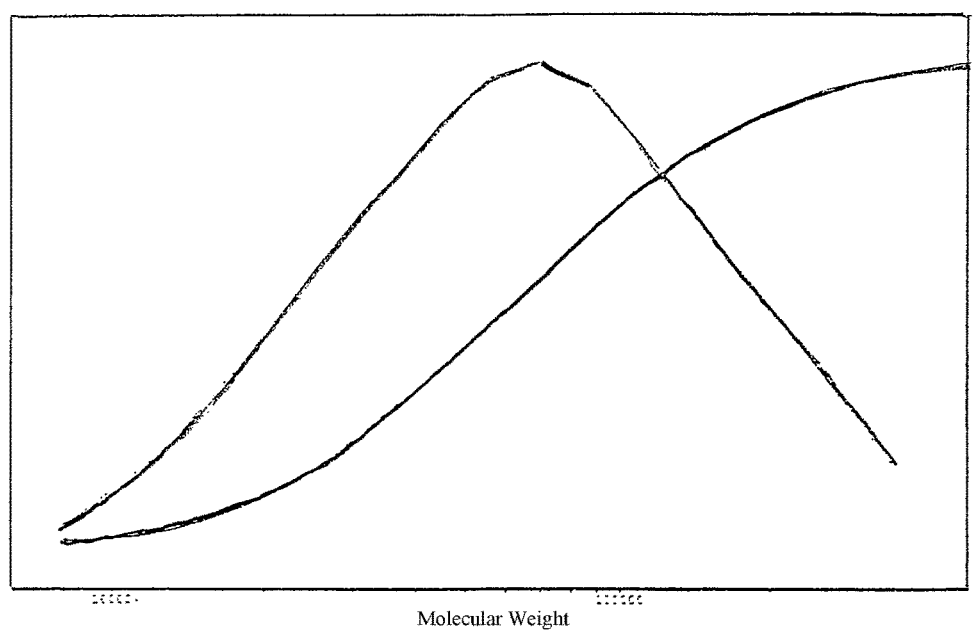
Figure 8:
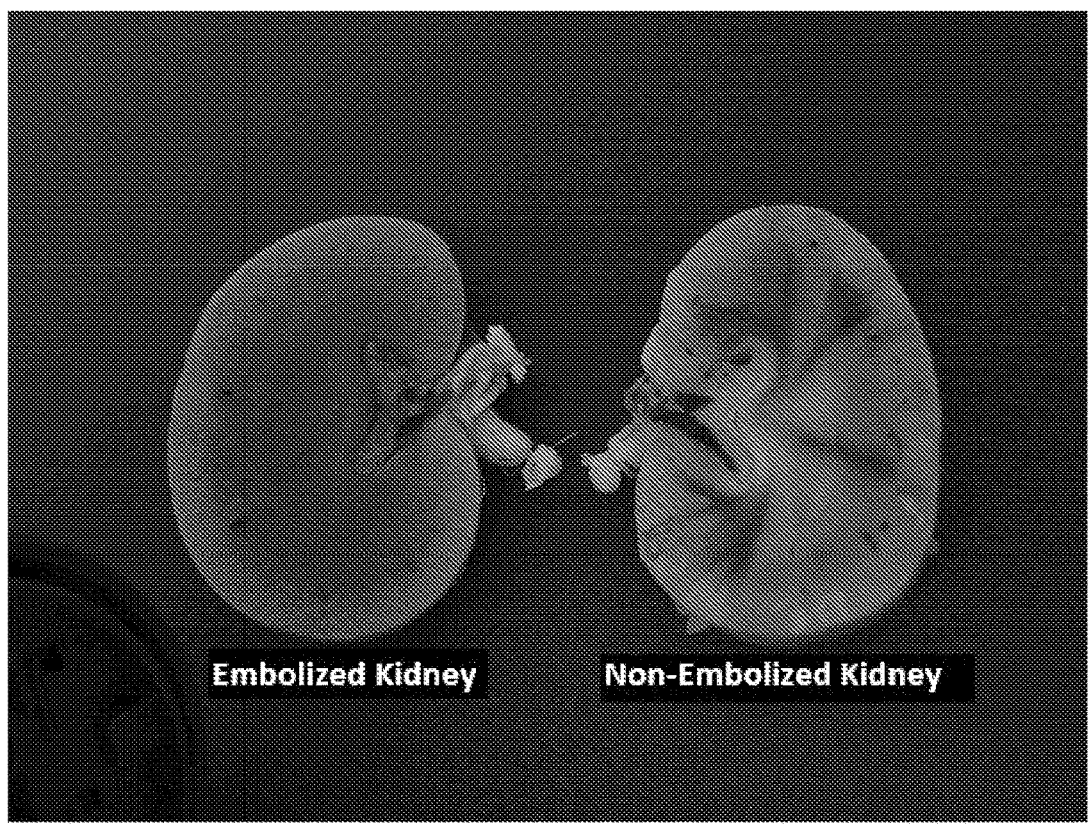
FIG. 8—Embolized kidneys with PVA/PVAc particles obtained in the Example 2 by 48 hours.
Figure 9:
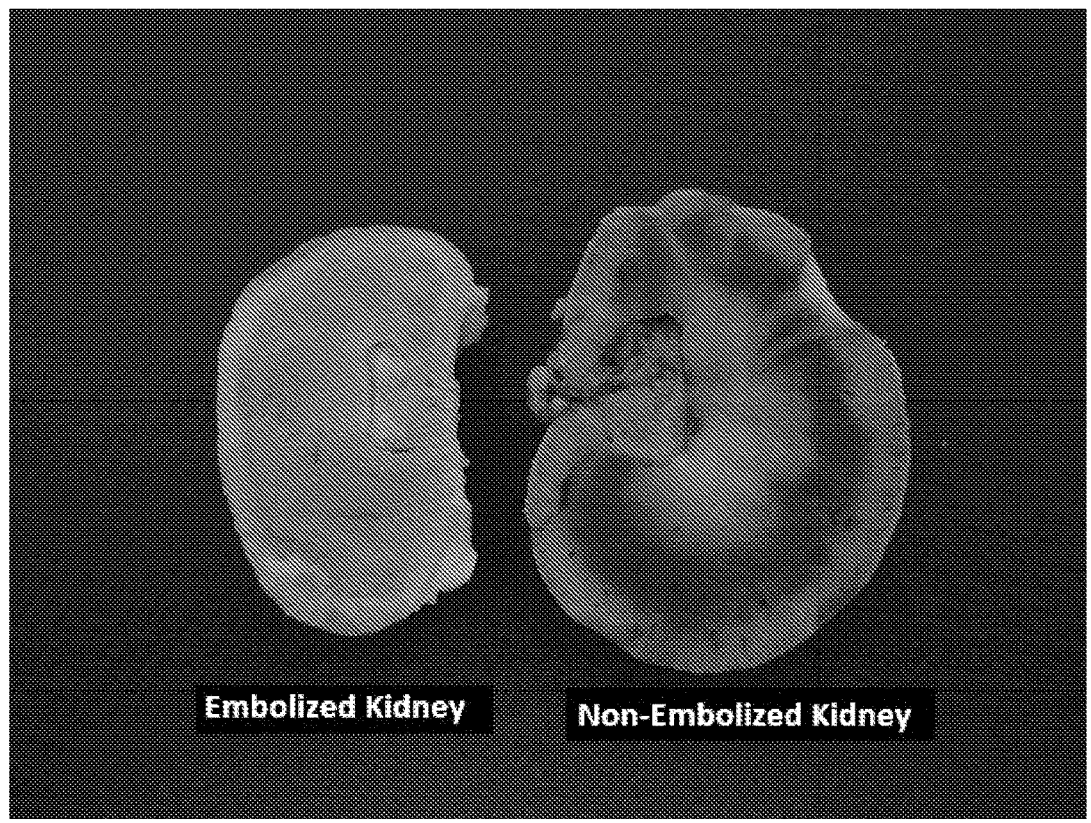
FIG. 9—Embolized kidneys with PVA/PVAc particles obtained in the Example 2 by 30 days.

The invention claimed is:

1. A process for the synthesis of poly (vinyl alcohol) and/or polyvinyl (acetate) with spherical morphology and shell-and-nucleus structure, the process being polymerization and in-situ saponification steps consisting of:
   polymerization in suspension, performed by loading a mixture consisting of a monomer component, distilled water; an initiator, a suspension agent, and one or more organic solvents selected from the group consisting of tert-butanol, n-hexane, and toluene, into an agitated reactor and allowing a reaction to take place for a period of time at a certain temperature, wherein:
   the concentration of the suspension agent is from greater than 0 to 2 g/L of water, the suspension agent is at least one or more of poly(vinyl alcohol), hydroxy-cellulose derivatives, and aliphatic polar polymers,
   the reaction temperature is in a range of from 20° C. to 90° C.,
   the amount of monomer component is in a range of from 10 to 50% by weight relative to the total weight of the mixture, the monomer component being at least one of vinyl acetate and one or more other vinyl monomers which are one or more of acrylic acid and its derivatives, methacrylic acid and its derivatives, and styrene and its derivatives, the amount of vinyl acetate in the monomer component being in a range from 0 to 100% by weight relative to the total weight of the monomer component,
   the concentration of initiator is from greater than 0 to 50 g/L of monomer component, the initiator being a free-radical generator that is one of benzoyl peroxide, lauroyl peroxide, and azo-bis-isobutironitrile,
   the agitation speed of the reactor is in a range from 100 to 5000 rpm, as particle sizes change with the agitation speed, and
   the reaction time is in a range from 0.5 to 12 hours, as monomer conversion changes with time;
   performing a caustic treatment in situ for a period of time in the same said reactor, the caustic treatment being saponification consisting of adding a volume of a caustic solution of a strong base directly to the reacted mixture in said reactor after the end of the polymerization reaction time and allowing the caustic treatment to take place for a period of time at a certain temperature, wherein:
   the caustic solution does not include methanol;
   the volume of caustic solution is in a range of from more than 0 to 200% of the initial volume of the aqueous phase,
   the concentration of the caustic solution is in a range of from more than 0 to 60% by weight,
   the agitation speed of the reactor is in a range from 100 to 5000 rpm, as in the polymerization step,
   the reaction temperature is in a range from 20° C. to 90° C., as in the polymerization step,
   the saponification time is in a range from more than 0 to 12 hours as in the polymerization step; and
   washing final PVA/PVAc particles obtained with shell-and-nucleus morphology with water and filtrating the washed particles under a vacuum,
   wherein the particles have spherical morphology and shell-and-nuclei structure, with granulometric distribution in a range from 20 μm to 1000 μm.

2. The process according to claim 1, wherein the suspension agent is an aqueous solution of poly (vinyl alcohol) in a concentration from 0.5 to 1 g/L.

3. The process according to claim 1, wherein the reaction temperature is in a range of from 65° to 75° C.

4. The process according to claim 1, wherein the monomer component is pure vinyl acetate in a concentration from 20 to 40% by mass of the suspension.

5. The process according to claim 1, the concentration of the initiator is in a range of from 5 to 15 g/L.

6. The process according to claim 1, wherein the temperature is kept constant and the suspension is kept under continuous agitation in a range of from 500 to 1500 rpm.

7. The process according to claim 1, wherein the reaction time is in a range of from 2 to 4 hours.

8. The process according to claim 1, wherein the saponification time is in a range of from 1 to 5 hours.

9. The process according to claim 1, wherein the volume of the caustic solution is in a range of from 50 to 100%.

10. The process according to claim 1, wherein the concentration in mass of the strong base is in a range of from 20 to 40%.

11. The process according to claim 1, wherein the suspension is left under continuous agitation in a range of from 500 to 1500 rpm.

12. The process according to claim 1, wherein the reaction temperature is in a range of from 25 to 35° C.

13. The process according to claim 1, wherein the reaction time is in a range of from 1 to 5 h.

14. The process according to claim 1, wherein the steps of polymerization and saponification are simultaneous.

15. The process according to claim 1, wherein the steps of polymerization and saponification are in sequence.

16. The process according to the claim 1, characterized for final superficial treatment of particles through an aqueous solution consisting of one or more organic compounds partially water soluble, being themselves kept under agitation in a range of from 50 to 5000 rpm, and temperature in a range from 0 to 50° C., constant and for a period of time in a range from 0 to 12 hours, being the organic material distributed on the new-formed particles surface.

17. The process according to the claim 1, wherein the VAc monomer contains vinylic comonomers.

18. The process according to the claim 1, wherein the suspension includes light and/or photosensitive indicators.

19. The process according to claim 18, including using ultra-violet light to induce the formation of free radicals.

20. The process according to the claim 18, including using luminous and/or radioactive radiation during the polymerization process, thereby reducing the operation temperature and simultaneously increasing the reaction velocity and modifying the final polymeric material properties including the molecular weight distribution.

21. Poly (vinyl alcohol) and/or polyvinyl (acetate) particles comprising particles obtained according to the process of claim 1, wherein the particles have specific area in a range of from 0 to 40 m$^2$/g, with molecular weight distribution in a range from 20×10$^3$ to 800×10$^3$ g/mol, with PVA shell occupying from 0 to 100% of the spherical calota, and consisting of an organic agent of superficial treatment that is one of gelatin, albumin, hydroxymethyl cellulose, poly (vinyl-pyrrolidone).

22. The poly (vinyl alcohol) and/or polyvinyl (acetate) particles according to claim 21, wherein the granulometric distribution is in a range of from 50 to 350 μm.

23. The poly (vinyl alcohol) and/or polyvinyl (acetate) particles according to claim 21, wherein the molecular weight distribution obtained after classification in separators is narrow.

24. The poly (vinyl alcohol) and/or polyvinyl (acetate) particles according to claim 21, wherein the specific area is in a range from 0 to 10 m$^2$/g.

25. The poly (vinyl alcohol) and/or polyvinyl (acetate) particles according to claim 21, wherein the average weighted molecular weight is in a range of from 50×10$^3$ to 250×10$^3$.

26. The poly (vinyl alcohol) and/or polyvinyl (acetate) particles according to claim 21, wherein a PVA percentage is in a range of from 10 to 30% in mass.

27. The poly (vinyl alcohol) and/or polyvinyl (acetate) particles according to claim 21, including a superficial treatment agent.

28. The poly (vinyl alcohol) and/or polyvinyl (acetate) particles according to claim 21, the particles being sterilized by radiation or thermal treatment in autoclave.

29. The process according to the claim 1, wherein the amount of organic solvent is in a range from greater than 0 to 50% by weight relative to the total weight of the monomer component.

30. The process according to the claim 29, wherein the organic solvent is tert-butanol in a concentration from greater than 0 to 10% by weight.

31. The process according to the claim 29, wherein the organic solvent includes a mixture of solvents.

32. The process according to claim 1, wherein the saponification step is performed after the polymerization step.

* * * * *